(12) United States Patent
Moskowitz et al.

(10) Patent No.: US 7,172,571 B2
(45) Date of Patent: Feb. 6, 2007

(54) APPARATUS AND METHOD FOR RETROGRADE PLACEMENT OF SAGITTAL SINUS DRAINAGE CATHETER

(75) Inventors: Ari Moskowitz, Santa Barbara, CA (US); Leanne Lintula, Santa Barbara, CA (US)

(73) Assignee: Medtronic, Inc., Minneapolis, MN (US)

( * ) Notice: Subject to any disclaimer, the term of this patent is extended or adjusted under 35 U.S.C. 154(b) by 16 days.

(21) Appl. No.: 10/698,334

(22) Filed: Oct. 31, 2003

(65) Prior Publication Data

US 2005/0096580 A1    May 5, 2005

(51) Int. Cl.
*A61M 5/00* (2006.01)
*A61M 31/00* (2006.01)
*A61M 25/16* (2006.01)

(52) U.S. Cl. .............................. 604/9; 604/8; 604/508; 604/537

(58) Field of Classification Search .............. 604/8–10, 604/264, 523, 540–541, 533, 537, 538, 500, 604/507, 508, 164.01, 164.02, 164.09, 167.01, 604/167.02, 167.03; 128/898; 606/108; 600/585
See application file for complete search history.

(56) References Cited

U.S. PATENT DOCUMENTS

| | | | |
|---|---|---|---|
| 2,969,066 A | 1/1961 | Holter et al. | |
| 3,020,913 A | 2/1962 | Heyer | |
| 3,288,142 A | 11/1966 | Hakim | |
| 3,894,541 A | 7/1975 | El-Shafei et al. | |
| 5,156,592 A * | 10/1992 | Martin et al. | 604/43 |
| 5,176,627 A | 1/1993 | Watson | |
| 5,385,541 A * | 1/1995 | Kirsch et al. | 604/8 |
| 5,520,632 A | 5/1996 | Leveen et al. | |
| 5,634,894 A | 6/1997 | Magram et al. | |
| 5,662,600 A * | 9/1997 | Watson et al. | 604/8 |
| 5,980,480 A | 11/1999 | Rubenstein et al. | |
| 6,283,934 B1 * | 9/2001 | Borgesen | 604/9 |
| 2002/0045847 A1 * | 4/2002 | Borgesen | 604/9 |
| 2002/0128588 A1 | 9/2002 | Borgesen | |
| 2004/0073154 A1 * | 4/2004 | Borgesen | 604/8 |

FOREIGN PATENT DOCUMENTS

WO    WO 98/11934    3/1998

OTHER PUBLICATIONS

Medline plus® Health Information, Medical Encyclopedia: "CSF leak" Definition 2002 pp. 1-2 http://www.nlm.nih.gov/medlineplus/ency/article/001068.htm.

(Continued)

*Primary Examiner*—Patricia Bianco
(74) *Attorney, Agent, or Firm*—IPLM Group, P.A.

(57) ABSTRACT

A method of inserting a drainage catheter into a sagittal sinus having blood flow from an upstream to a downstream direction. A burr hole is created, if necessary, in the cranium of the patient proximate the sagittal sinus. A distal end of a catheter is inserted through the burr hole and the dura into the sagittal sinus. The distal end of the catheter is positioned so that the distal end points generally in the upstream direction with respect to the blood flow. A sagittal sinus catheter is adapted for placement through the dura of a patient proximate a superior sagittal sinus. The catheter is formed of semi-rigid material and has at least a ninety degree bend.

10 Claims, 6 Drawing Sheets

OTHER PUBLICATIONS

YouSurgery.Com®, "Shunt for Hydrocephalus, Complications", 2000 p. 7.
Gruen M.D., John Peter, Neurosurgery Infonet "Cerebrospinal fluid (CSF) leak" 2000 pp. 1-2 http://www.uscneurosurgery.com/glossary/c/csf%20leak.htm.
Capitol Anesthesiology Association, Services, Complications/Risks "Spinal Headache" p. 1 http://www.capanes.com/services_cr.html.
Gruen M.D., John Peter, Neurosurgery Infonet, Neurosurgical Procedures, Risks and Complications "Acoustic neuroma resection" pp. 1-9 http://www.uscneurosurgery.com/patient%20education/risks%20complications/procedure/risks%20complications%20acoustic%20removal.htm.
Krzysztof M. Kuczkowski, "Post-dural puncture syndrome in an elderly patient with remote history of previous post-dural puncture syndrome", Acta Anaesthesiol Scand 2002; 46: 1049-1050.
Medamicus Incorporated, Venous Introducers, Product Overview, "Venous Introducers and Vascular Delivery Systems" 2001 pp. 1-2 http://www.medamicus.com/venous.asp.
Tubbs, SR et al. "Sagittal Suture as an External Landmark for the Superior Sagittal Sinus" Journal of Neurosurgery, 2001 94:985-987.
Andrews, BT et al. "Microsurgical Anatomy of the Venous Drainage into the Superior Sagittal Sinus", 1989 24(4) 514-520.
Curé, JK, Van Tassels, P, Smith, MT "Normal and Variant Anatomy of the Dural Venous Sinuses" Seminars in Ultrasound, CT and MRI, 1994 15(6):499-519.
Hash, CJ et al. "Ventricle to Sagittal Sinus Shunt For Hydrocephalus" Neurosurgery, 1979 4(5): 394-398.
Svistov, DV "Pathology of the Sinuses and Veins of the Dura Mater" Department of Neurosurgery, Russian Military-Medical Academy, St. Petersburg, 16 pgs. www.neuro.neva.ru.
Nakagawa, H et al. "Papillary Meningioma Arising from the Confluens Sinuum with Multidirectional Extension through the Venous Sinuses" Surg Neurol. 1989 32:219-224.
Bavinzski, G et al. "Variant Arteriovenous Fistula of the Superior Sagittal Sinus" Neurol Med Chir (Tokyo) 1999 39:362-366.
Browder, J and Kaplan, HA "Venous Drainage Following Ablation or Occlusive Isolation of the Rostral Superior Saggital Sinus" Surg Neurol. 1973 1:249-251.
Petroni, S and Marrone, AC "Study of the Trabecular Projections (Chordae Willisii) of the Superior Sagittal Sinus" IT Journal Anat. Embroyl. 1997 102(3) 155-163.
Zilkha, A et al., "Computed Tomography of the Normal and Abnormal Superior Sagittal Sinus" Clinical Radiology 1982 33:415-425.
Oka, K et al. "Microsurgical Anatomy of the Superficial Veins of the Cerebrum" Neurosurgery 1985 17(5): 711-748.
Becker, DP, Jane, JA, and Nulsen, FE (1980). Investigation of sagittal sinus for venous shunt in hydrocephalus. *Surgical Forum, Neurological Surgery*, 440-442.

Børgesen, SE, Gjerris, F, and N Agerlin (2002). Shunting to the Sagittal Sinus. Acta Neurochir 8, 11-14.
El-Shafei, I & El-Shafei H (2001). The retrograde ventriculosinus shunt: concept and technique for treatment of hydrocephalus by shunting the cerebrospinal fluid to the superior sagittal sinus against the direction of blood flow. Preliminary Report. Child's Nerv Syst 17, 457-464.
El-Shafei, I & El-Rifaii, MA (1987). Ventriculojugular shunt against the direction of blood flow: I Role of the internal jugular vein as an antisiphonage device. Child's Nerv Syst 3, 282-284.
El-Shafei, I & El-Rifaii, MA (1987). Ventriculojugular shunt against the direction of blood flow: II Theoretical and experimental basis for shunting the cerebrospinal fluid against the direction of blood flow. Child's Nerv Syst 3, 285-291.
Kimber, J (2002) Cerebral venous sinus thrombosis. QJ Med 95, 137-142.
Okoro, BA, Ohaegbulam, SC (1995). Experience with Ventriculo Peritoneal Shunts at the University of Nigeria Teaching Hospital, Engug. East African Medical Journal, 72(5), 322-4.
Pásztor, A, Czirják, Pásztor, E (1982). Is the Ventriculo-Sagittal Sinus Shunt a Favourable Solution? Monogr. Paediatr., 15, 60-62.
Sharkey, PC (1965) Ventriculosagittal-Sinus Shunt. J Neurosurg 22, 362-266.
Wen, HL. (1982) Ventriculo-Superior Sagittal Sinus Shunt for Hydrocephalus. Surg Neurol 17, 432-434.
International Search Report cited in a foreign counterpart and mailed on Aug. 30, 2005, 2 pgs.
McCabe, W.L. Smith J.C. (1967) Fluid Flow Phenomenon, Ch. 3, $2^{nd}$ Ed., In: Unit Operations of Chemical Engineering, McGraw, New York, pp. 47-67.
El-Shafei, I.L., et al. (1987), Ventriculo-Jugular Shunt Against The Direction of Blood Flow, III, Operative Techniques and Results, Childs. Nervous System, 3:342-349.
El-Shafei, I.L., et al., (1991), Ventriculo-jugular Shunt Against the Direction of Blood Flow, IV, Technical Modifications and Policy for Treatment, Childs Nervous System, 7:197-204.
El-Shaarawy, AM (1997), Study of Alternative Methods for Cerebrospinal Fluid Shunting to the Venous Circulation, Experimental Modeling, A Thesis Submitted to the faculty of engineering at Cairo University in partial fulfillment of the requirements for the degree of Doctor of Philosophy in chemical engineering.
Pudenz R.H., Russell EE, Hard Ah, Cheldon, Ca. (1957), Ventriculo-Auriculostomy, A Technique for Shunting Cerebrospinal Fluid Into the Right Auricle, Preliminary Report J. Neurosurg., 14:171-179.
Noordergraaf AL (1978) Circulatory System Dynamics, Ch. 5, Academic Press, N.Y., London.

* cited by examiner

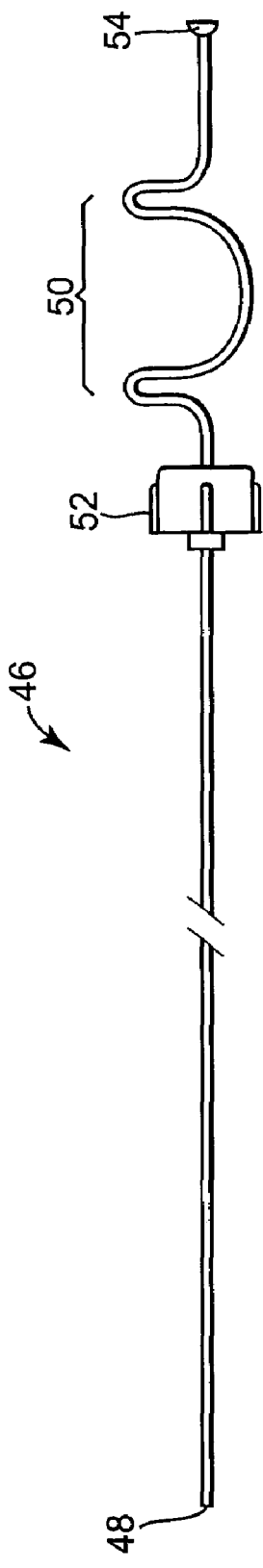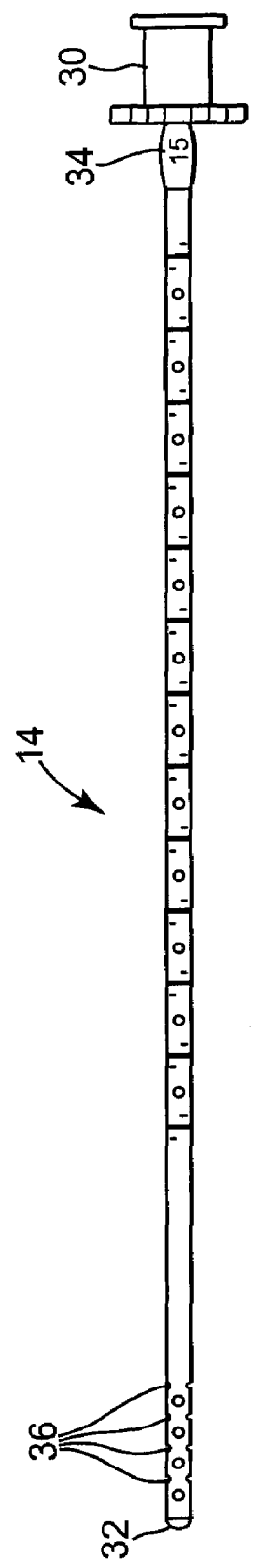
Fig. 7
Fig. 2

APPARATUS AND METHOD FOR RETROGRADE PLACEMENT OF SAGITTAL SINUS DRAINAGE CATHETER

FIELD OF THE INVENTION

The present invention relates generally to apparatus and methods for the introduction and placement of cranial catheters and, more particularly, to apparatus and methods for the introduction and placement of sinus catheters.

BACKGROUND OF THE INVENTION

Ventricles of the brain contain cerebrospinal fluid (CSF) which cushions the brain against shock. CFS is constantly being secreted and absorbed by the body usually in equilibrium. Cerebrospinal fluid is produced in the ventricles of the brain, where under normal conditions, it is circulated in the subarachnoid space and reabsorbed into the bloodstream, predominantly via the arachnoids villi attached to the superior sagittal sinus. However, if blockages in circulation of CSF, perhaps in the ventricles, CSF can't be reabsorbed by the body at the proper rate.

This can create a condition known as hydrocephalus which is a condition marked by an excessive accumulation of fluid violating the cerebral ventricles, then the brain and causing a separation of the cranial bones. Hydrocephalus is a condition characterized by abnormal flow, absorption or formation of cerebrospinal fluid within the ventricles of the brain which subsequently increases the volume and pressure of the intracranial cavity. If left untreated, the increased intracranial pressure can lead to neurological damage and may result in death.

Over the past 40 years, a common treatment for hydrocephalus patients has been the cerebrospinal fluid shunt. The standard shunt consists of the ventricular catheter, a valve and a distal catheter. The excess cerebrospinal fluid is typically drained from the ventricles to a suitable cavity, most often the peritoneum or the atrium. A catheter is tunneled into the brain through a burr hole in the skull. The catheter is placed into ventricles to shunt CSF to other areas of the body, principally the peritoneum, where it can be reabsorbed. The presence of the shunt relieves pressure from CSF on the brain.

A flow or pressure regulating valve is usually placed along the catheter path. Differences in pressure due, at least in part, to differences in vertical position between the inlet (ventricles) and the outlet (peritoneum) can create too much drainage with such a flow or pressure regulating valve.

An alternative, and newer, method to shunting CSF to the peritoneum is to shunt CSF from the ventricles to the sagittal sinus.

A conventional technique for placing a catheter in the ventricles in the brain is to first drill a burr hole in the skull. A scalpel can then be used to create a slit in the dura surrounding the brain to gain access. However, controlling the length of the slit in the dura is difficult and will vary from surgery to surgery.

An alternative method after first drilling a burr hole is to use cautery to heat/burn tissue of the dura to create and opening in the dura. Still, controlling the shape and diameter of the opening in the dura is difficult and, again, will vary from surgery to surgery.

The holes provided by the preceding techniques provide a pathway to the ventricles. A catheter is then intubated into the lateral ventricle which remains in place in the patient.

Both standard methods of entry allow for leakage of CSF around the outer surface or diameter of the catheter from the dura post-implant. Leakage of CSF through the dura can cause serious surgical complications including infection, severe headaches and disturbances of hearing or vision. It can also lead to changes in pressures of fluid in the ventricular/shunt system and result in complications and failures. It has been estimated that approximately forty percent (40%) of initial ventricular shunt installations require correction or revision.

The shunt implantation procedure is associated with the known incidents of complications that are recognizable and treatable. Of these, ventricular catheter obstruction is the most common reason for revision followed by infection. When shunting from the ventricles to the venous system, either via the right auricle or the dural sinuses, thromboembolic complications and the dissemination of infection through the bloodstream are additional risks.

Shunting can also be accomplished from the ventricles to the sagittal sinus, particularly the superior sagittal sinus. This procedure involves making a second entry into the cranium in order to install an outlet catheter into the sagittal sinus. Placing a distal catheter in the blood stream of the sagittal sinus creates the potential for blood clotting and resulting occlusion of the sinus passageway.

BRIEF SUMMARY OF THE INVENTION

The present invention provides apparatus and methods for introducing and placing a catheter placed through the dura in order to accomplish a shunting into the sagittal sinus.

In one embodiment, the present invention provides a method of inserting a drainage catheter into a sagittal sinus of a patient. The sagittal sinus has blood flow from an upstream to a downstream direction. A burr hole is created in the cranium of the patient proximate the sagittal sinus, if necessary. A distal end of a catheter is inserted through the dura into the sagittal sinus. The distal end of the catheter is positioned so that the distal end points generally in the upstream direction with respect to the blood flow.

In another embodiment, the present invention provides a sagittal sinus shunt. A catheter has a ventricle portion and a sinus portion. The ventricle portion is adapted for placement into a cranium of a patient proximate a ventricle and the sinus portion is adapted for placement into the cranium of the patient proximate a superior sagittal sinus. A valve is operatively coupled in the catheter between the ventricle portion and the sinus portion. The sinus portion of the catheter has at least a ninety degree bend.

In another embodiment, the present invention provides a sagittal sinus catheter adapted for placement into said cranium of said patient proximate a superior sagittal sinus. The catheter is formed of a semi-rigid material. The catheter has at least a ninety degree bend aiding insertion in the retrograde direction and limiting the depth of insertion.

Positioning the discharge end of the sinus catheter in the retrograde facing the upstream flow of blood in the sagittal sinus helps the sinus catheter to prevent thrombosis. The collision of CSF flowing outward in an upstream direction in the sagittal sinus helps to prevent blood flowing in the sagittal sinus from forming a wake at the discharge point and possibly creating blood clotting conditions.

Further, the present invention is easy to use and provides important time savings in use by the surgeon. Minimizing surgical time provides important safety benefits for the patient.

BRIEF DESCRIPTION OF THE DRAWINGS

FIG. 2 is a side view of a ventricular catheter used in the shunt system illustrated in FIG. 1;

FIG. 7 is a side view of a ventricular catheter stretcher used in installation used of the shunt system illustrated in FIG. 1;

DETAILED DESCRIPTION OF THE INVENTION

Figure 1:
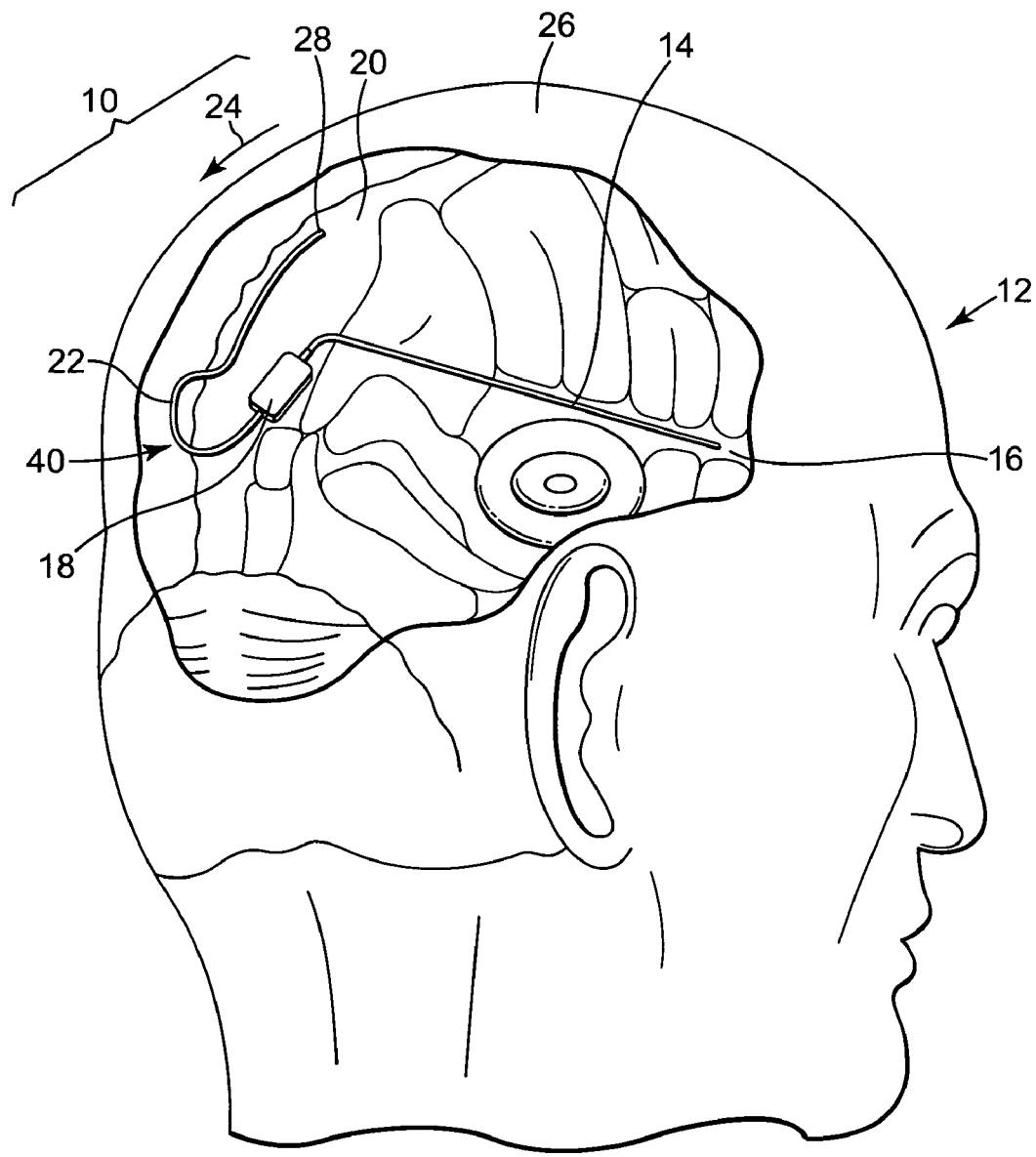
FIG. 1 is an illustration of a shunt system in accordance with certain embodiments of the present invention installed in the cranium of a patient.

The various embodiments of the present invention can be understood by reference to the shunt system 10 illustrated in FIG. 1 which shows the ventricular to sagittal sinus shunt system 10 in place in a patient 12. Ventricular catheter 14 has been inserted through a burr hole (not shown) into the lateral ventricle 16 of patient 12. Ventricular catheter 14 is coupled to valve 18 which controls the flow of CSF from lateral ventricle 16 to sagittal sinus 20. Valve 18 is also coupled to sinus catheter 22 shown inserted through another burr hole (also not shown) into the superior sagittal sinus 20.

Shunt system 10 allows excess CSF present in lateral ventricle 16 to flow through ventricular catheter 14, valve 18 and sinus catheter 22 into the blood stream of sagittal sinus 20 where the excess CSF can be reabsorbed into the body. The vertical distance between the location of ventricular catheter 14 and sinus catheter 22 is small compared with vertical distance usually associated with a peritoneum catheter leading to smaller pressure differences due to gravitation between the inlet catheter, ventricular catheter 14, and the outlet catheter, sinus catheter 22.

Blood flow in sagittal sinus 20 is generally from in the direction shown by arrow 24 from the frontal portion of cranium 26 of patient 12 to the rear portion of cranium 26 of patient 12. In a preferred embodiment, distal end 28 sinus catheter 22 has a retrograde orientation in sagittal sinus 20, essentially pointing upstream against the flow of blood in sagittal sinus 20 shown by blood flow arrow 24. Positioned in this manner, outlet of CSF from distal end 28 of sinus catheter 22 provides a collision vortex in the flow of blood around sinus catheter 22. This retrograde position provides a substantial decrease in the likelihood of thrombosis resulting from an ante grade position of distal end 28 of sinus catheter 22 in the wake created by sinus catheter 22 of the bloodstream in sagittal sinus 20.

Figure 8:
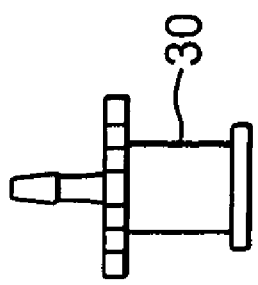
FIG. 8 is a side view of a female luer used in an embodiment of a ventricular catheter used in the shunt system illustrated in FIG. 1.

Ventricular catheter 14 is illustrated more clearly in FIG. 2 coupled with female luer 30 (also shown in FIG. 8). Ventricular catheter 14 is an extensible elongate body having distal end 32 and proximal end 34. Distal end 32 of ventricular catheter 14 is inserted into lateral ventricle 16 of cranium 26 of patient 12 as will be discussed below. Ventricular catheter 14, shown in a relaxed state, has an outside diameter of 2.5 millimeters and a length of 15 centimeters. Ventricular catheter 14 has a lumen with a diameter of 1.3 millimeters (relaxed state). Distal end 32 contains outlets 36 from the lumen consisting of four rows of four holes each extending approximately 1 centimeter from distal end 32. Ventricular catheter 14 has 13 length markers in one centimeter spacing from 3 centimeters to 15 centimeters from proximal end 34 including numerical length markers at 5, 10 and 15 centimeters. Such length markers aid the surgeon in determining how deeply ventricular catheter 14 is placed. Female luer 30 is sewn onto proximal end 34 of ventricular catheter 14. Ventricular catheter 14 is formed of an extensible material such as silicone elastomer tubing having a durometer of fifty (50) and an elongation of four hundred fifty percent (450%). Ventricular catheter 14 has a tensile strength of 900 pounds per square inch.

Figure 3A:
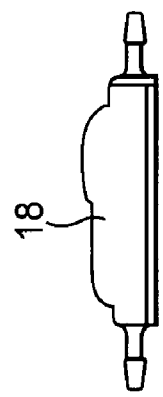
FIG. 3A is a top view of a valve used in the shunt system illustrated in FIG. 1.
Figure 3B:
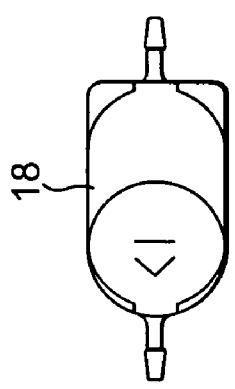
FIG. 3B is a side view of a valve used in the shunt system illustrated in FIG. 1.

Valve 18 (FIG. 3A and FIG. 3B) is a one-way check valve approximately 20 millimeters long, 11 millimeters wide and 4 millimeters high. Valve 18 only ensure one way flow from ventricle 16 to sagittal sinus 20 and doesn't regulate the rate of flow of CSF.

Figure 4:
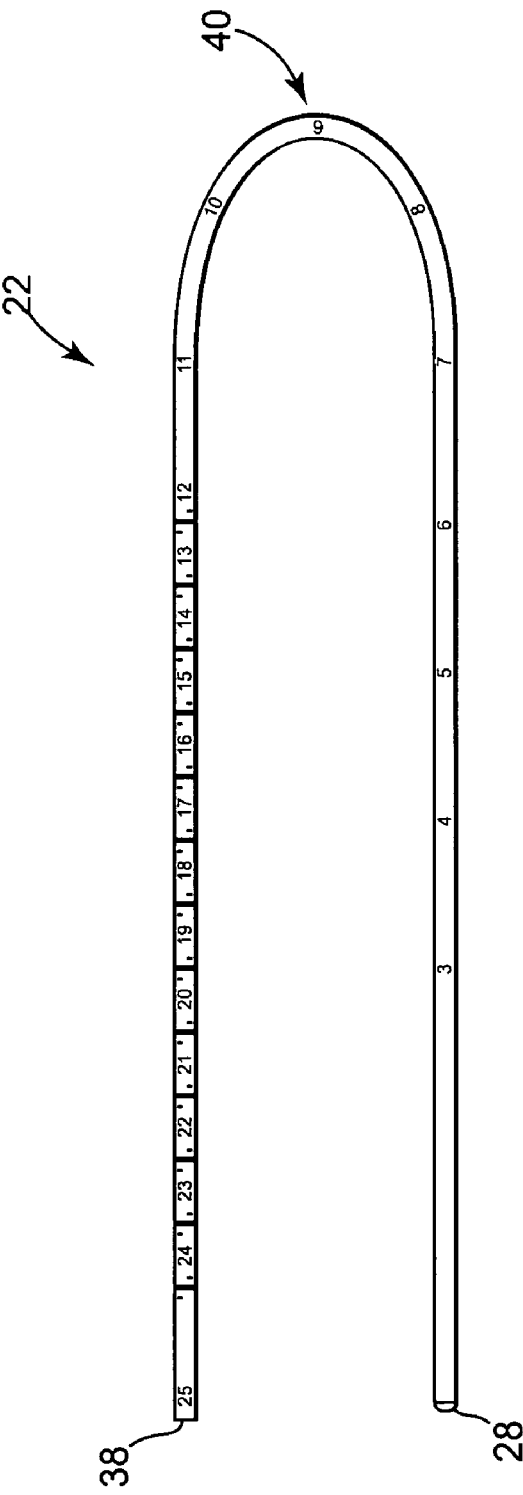
FIG. 4 is a side view of a sinus catheter used in the shunt system illustrated in FIG. 1.

Sinus catheter 22 in FIG. 4 has distal end 28 having a smooth open-ended tip and proximal end 38. Sinus catheter 22 is formed of a semi-rigid material such as silicone elastomer tubing having a durometer of eighty (80) with an outside diameter of 2.1 millimeters and a length of 25 centimeters. Sinus catheter 22 has a lumen with a diameter of 1.2 millimeters. Sinus catheter 22 has 23 numeric length markers in one centimeter spacing from 3 centimeters to 25 centimeters from distal end 28.

In order to properly insert sinus catheter 22 in a retrograde position in sagittal sinus 20, sinus catheter 22 has bend 40 located approximately seven (7) centimeters from distal end 28. As is shown in FIG. 1, bend 40 allows sinus catheter 22 to lie smoothly against head of patient 12 once inserted into sagittal sinus 20. Bend 40 actually makes it difficult for the surgeon to insert sinus catheter 22 in a position other than retrograde essentially ensuring proper placement of sinus catheter 22 in sagittal sinus 20. While bend 40 is illustrated to be approximately a one-hundred eighty degree bend, other degrees of bend are possible and contemplated. Bend 40 alternatively could be a ninety degree bend and achieve similar results. It is preferred that bend 40 be at least a ninety degree bend.

Shunt system 10 is installed by first drilling a burr hole in cranium 26 using a conventional technique. In some patients, such as small children and/or infants, a burr hole may not be necessary. A parieto occipital skin flap is mapped to expose the sites of sinus exposure and the dural hole for ventricular catheter 14 insertion into lateral ventricle 16. The sinus will be exposed anterior to the external occipital protuberance and the opening to penetrate the ventricle 16 will be made lateral and slightly anterior to the exposed sinus, in line with the lateral ventricle 16. Two separate curvilinear small incisions may be used instead of the skin flap in patients above six years of age, to access the superior sagittal sinus 20 and lateral ventricle 16, respectively. Alternatively, a frontal approach to access lateral ventricle 16 could be used.

After reflection of the scalp, the tissue is incised over the sites chosen for the bony openings exposing the superior sagittal sinus 20 and cerebral ventricles, respectively.

The superior sagittal sinus 20 is exposed through a burr hole centered over the sagittal suture. The burr hole may be widened to expose the sinus fully, which in some instances may deviate slightly to the right of the sagittal suture, and bevel its posterior edge.

Figure 5:
FIG. 5 is a side view of a right angle clip used in the shunt system illustrated in FIG. 1.

A burr hole may be made in line with the lateral ventricle 16, exposing a circle of dura mater. If right angle clip 42 (FIG. 5) is not used, it is recommended that the posterior rim of the burr hole be beveled where catheter 14 emerges and curves to lie adjacent to the skull. A subgaleal pocket should be formed with appropriate depth to accept the extracranial portion of the ventricular catheter 14 and valve 18.

Figure 6:
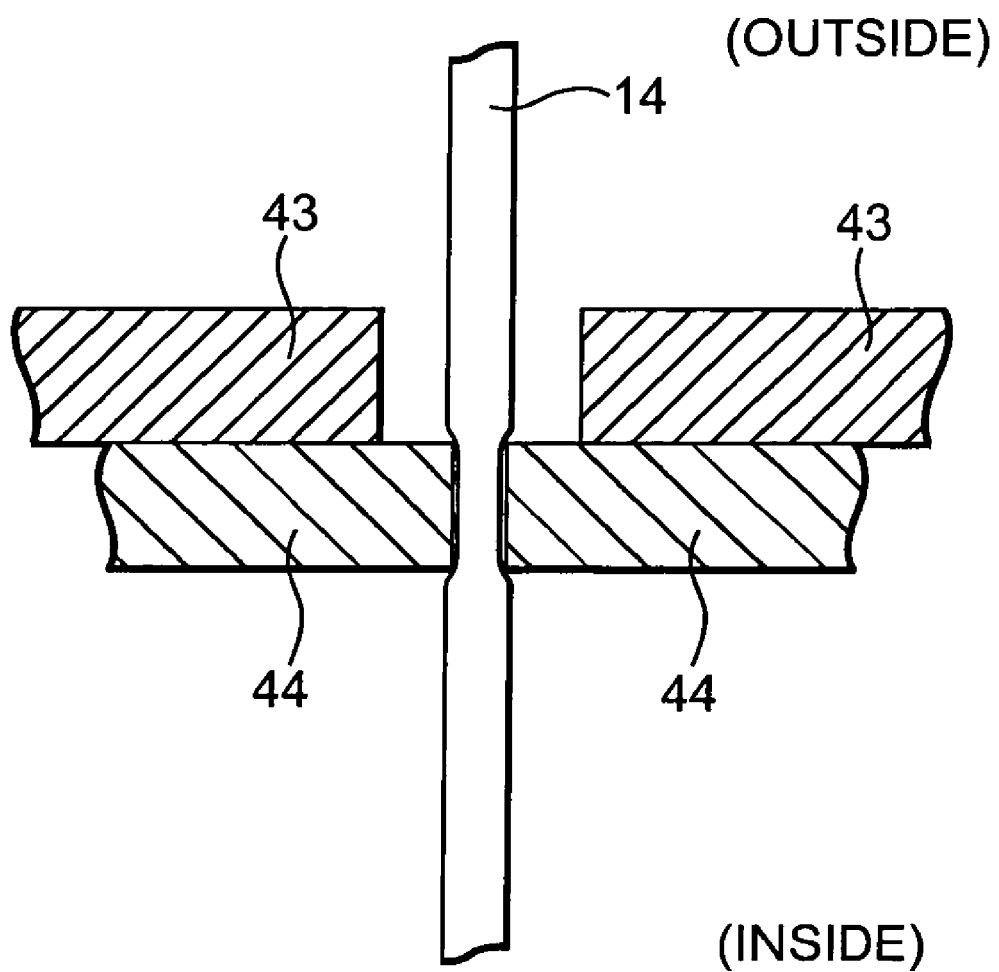
FIG. 6 is a cross-sectional view a ventricular catheter inserted into a dural hole formed in accordance with embodiments of the present invention.

A burr hole will be made in skull 43 at the point of insertion of ventricular catheter 14. A hole also will be made in the dura having predetermined diameter as illustrated in FIG. 6. In order to help control CSF leakage cranium 26, ventricular catheter 14 is stretched from its relaxed state prior to insertion through dura 44. A hole with a precise diameter is made in dura 44 which, preferably, is approximately the diameter of ventricular catheter 14 in its relaxed state. In order to be able to insert ventricular catheter 14 through dura 44, ventricular catheter 14 is stretched in a controlled manner in order to reduce its outside diameter to a diameter which is less than the controlled diameter of the hole made in dura 44. Ventricular catheter 14 is inserted through dura 44 in its stretched state allowing easy insertion. Following insertion, ventricular catheter 14 reverts to its relaxed state allowing its outside diameter to return to approximately equal to or smaller than its original relaxed state diameter and essentially filling the hole in dura 44. Having a controlled shape and diameter for the hole created in dura 44 allows ventricular catheter, once inserted, to mostly fill and seal the hole in dura 44 helping to prevent or control leakage of CSF from inside cranium 26.

Catheter stretcher 46 (FIG. 7) can be utilized to controllably stretch ventricular catheter 14 to a stretched state in which the outside diameter of ventricular catheter has been made smaller to allow ventricular catheter 14 to be easily inserted through a controlled diameter hole in dura 44. Catheter stretcher 46 consists of an elongate rod having a diameter smaller than the diameter (1.3 millimeters) of the lumen of ventricular catheter 14 allowing distal end 48 to be inserted through female luer 30 into lumen of ventricular catheter 14. Distal end 48 of catheter stretcher 46 penetrates the lumen of ventricular catheter completely with distal end 48 of catheter stretcher resting against distal end 32 of ventricular catheter 14. Curves 50 in catheter stretcher 46 make catheter stretcher 46 easier to handle. Luer cap 52 is affixed on catheter stretcher 46 a distance away from distal end 48 which is greater than the distance between distal end 32 of ventricular catheter 14 and female luer 30. Once catheter stretcher 46 is inserted completely into lumen of ventricular catheter 14, female luer 30 is grasped and pulled up and mated with luer cap 52. The amount that distance between distal end 48 and luer cap 52 exceeds the distance between distal end 32 and female luer 30 is the controlled amount which ventricular catheter 14 is stretched. As ventricular catheter 14 is stretched its outside diameter becomes smaller.

Catheter stretcher 46 also provides ventricular catheter 14 with stiffness to aid in insertion of ventricular catheter 14 into lateral ventricle 16.

A small hole with a diameter greater than outer diameter of ventricular catheter 14 in its stretched state and less than outer diameter of ventricular catheter 14 in its relaxed state is made in the center of exposed dura mater 44.

Catheter stretcher 46 has, at its proximal end, tip 54 which is sized and shaped at a desired diameter for the dural hole. Preferably, this diameter is greater than outer diameter of ventricular catheter 14 in its stretched state and less than outer diameter of ventricular catheter 14 in its relaxed state. Preferably, tip 54 is hemispherically shaped.

Once the dura has been exposed, tip 54 can be applied against the dura and a diathermy current applied to catheter stretcher 46, typically by touching a cautery needle to the shank of catheter stretcher 46 near tip 54 in order to cauterize dura 44 creating a hole in dura 44 of the precise size and shape of tip 54. Since tip 54 is sized and shaped to the desired size and shape of the dural hole, tip 54 need not be manipulated to manually create a hole of a size larger than a cautery tip typically used. Such undesirable manual manipulations tend to create irregular and unevenly sized holes which vary from surgery to surgery.

Right angle clip 42 on ventricular catheter 14 can be used as a marker for planned depth of ventricular catheter 14 insertion by sliding it the desired distance from proximal end 34 of ventricular catheter 14 prior to insertion.

Stretched ventricular catheter 14 is introduced into the lateral ventricle 16 through the dural opening (the direction of ventricular catheter insertion is along a line extending from the dural hole to the ipsilateral pupil) into the anterior horn. The position of the catheter stretcher (stylet) is maintained with one hand and luer cap 52 is unlocked with the other hand allowing ventricular catheter to relax to its original diameter without retracting from ventricle 16. Ventricular catheter 14 should fit snugly in the dural hole, helping to hermetically seal it. Imaging may be used to verify proper placement of the catheter.

Figure 9:
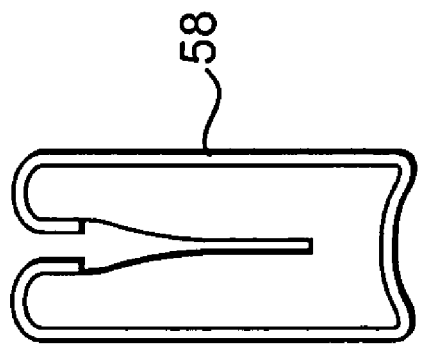
FIG. 9 is a side view of a clamp used in installation of the shunt system illustrated in FIG. 1.

The stylet (catheter stretcher) 46 is removed and ventricular catheter is clamped (with clamp 58 shown in FIG. 9) immediately after the withdrawal of stylet 46 to help prevent CSF loss.

Right angle clip 42 on ventricular catheter 14 may be used to bend ventricular catheter 14 to an approximate ninety degree angle where it exits the twist drill or burr hole. The extracranial portion of ventricular catheter is pressed into the split tubular segment of right angle clip 42 to form a right angle bend. Stretching of ventricular catheter 14 is avoided when it is pressed into right angle clip 42. It is recommended that right angle clip 42 be secured to adjacent tissue by passing sutures through the two suture flanges on the sides of right angle clip 42.

A clamp is removed as necessary and saline is injected into ventricle 16 through ventricular catheter 14 to replace lost CSF and to clear any tissue debris, to raise the CSF pressure and to help make sure that there is not leakage from around ventricular catheter 14.

The extra length of ventricular catheter 14 is cut off so that only two to three centimeters of ventricular catheter 14 remain projecting outward from the burr hole.

The inlet port of valve 18 is fit into the open end of ventricular catheter 14 and is secured by a suture.

The clamp is momentarily removed on ventricular catheter 14 to prime valve 18 and to remove air bubbles. The clamp is reapplied to ventricular catheter 14.

After exposing the roof of the sinus by direct observation or needle puncture, an opening is made through the dural roof of the sinus 20 large enough to accommodate sagittal sinus catheter 22. A finger is applied on the sinus 20 at the puncture site to prevent excessive blood loss.

Distal end 28 of sinus catheter 22 is introduced into sagittal sinus 20 and advanced forward against the direction of blood flow for a distance of approximately five centimeters. If any obstacle to the free passage of sinus catheter 22 is encountered, the sinus catheter 22 is withdrawn a bit and redirected in its advance into sagittal sinus 20. Sinus catheter 22 is advanced slightly and retracted to approximately five centimeters to provide additional assurance that sinus catheter 22 resides in the main sagittal sinus 20 lumen.

After placement of sinus catheter 22, good blood flow is checked by allowing venous back flow into the unclamped sinus catheter 22. After establishing venous back flow, saline is injected into sinus catheter 22 to clear blood from sinus catheter 22. The sinus catheter 22 is clamped. Any bleeding from around sinus catheter 22 should be controlled, e.g., by gel foam, pressure and/or suture.

The proximal end 38 of sinus catheter 22 is formed in a smooth U-curve to the outlet of valve 18. The required length of proximal end 38 of sinus catheter 22 is estimated, the position of the clamp on sinus catheter 22 is adjusted and the extra sinus catheter 22 is cut off.

The outlet port of valve 18 is fit into proximal end (having been cut off) of sinus catheter 22 and secured by a suture. Valve 18 is secured by suture to the underlying pericranium.

The clamps on ventricular catheter 14 and sinus catheter are removed, respectively, allowing CSF to flow in shunt system 10. The skin is closed in the usual manner.

Figure 10:
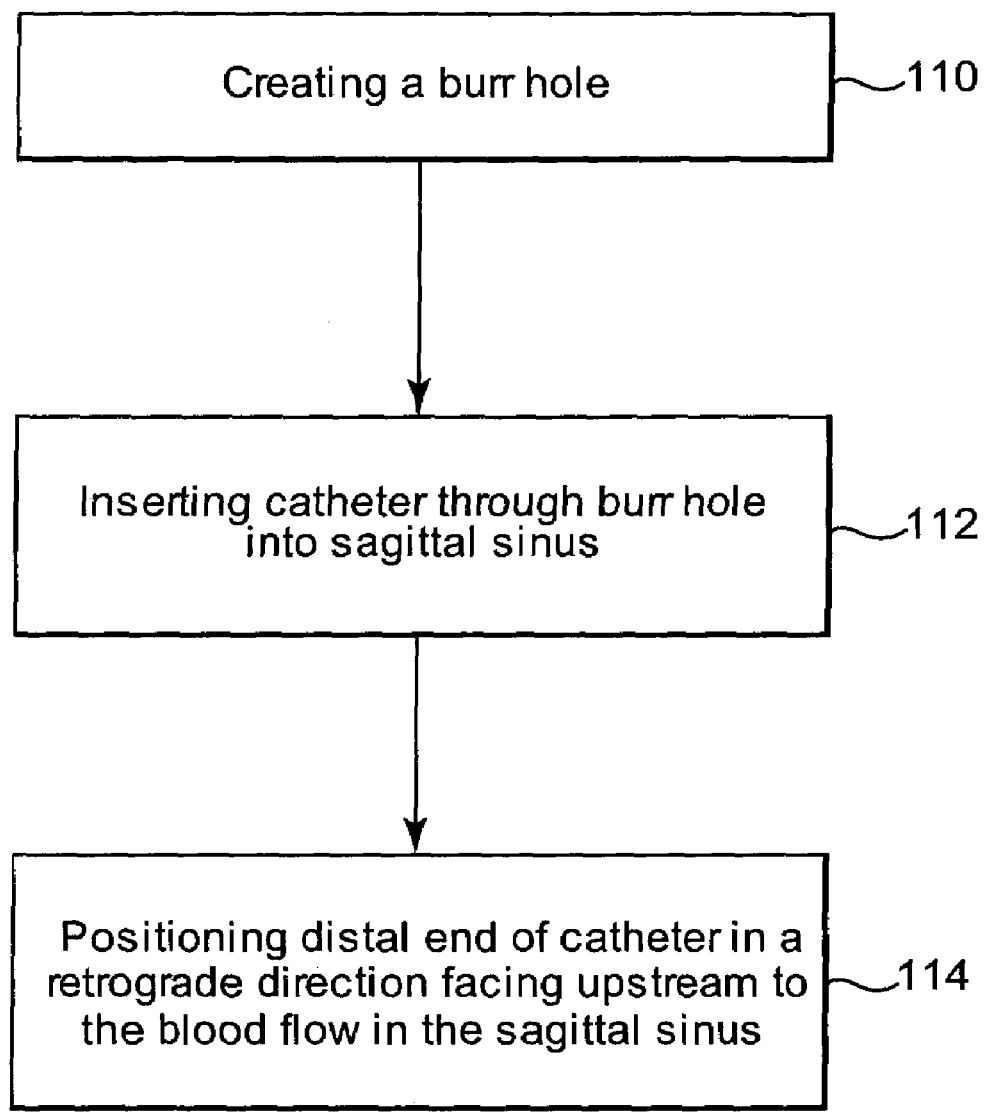
FIG. 10 is a flow of a method of an embodiment of the present invention.

A method of an embodiment of the present invention is illustrated in FIG. 10. A burr hole is created (110) in the cranium 26 of the patient 12, if necessary. A catheter, such as sinus catheter 22, is inserted (112) through the dura into the sagittal sinus 20. The distal end of the catheter 22 is positioned in a retrograde direction facing upstream to the blood flow in the sagittal sinus 20.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to shunt systems but could employed in other systems involving holes in the dura. The present invention is not limited to the apparatus described herein per se, but may find further application in other medical areas. The present invention further includes within its scope methods of making and using the apparatus described hereinabove.

Thus, embodiments of the apparatus and method for retrograde placement of sagittal sinus drainage catheter are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method of inserting a drainage catheter into a sagittal sinus of a patient having a cranium, said sagittal sinus having blood flow from an upstream to a downstream direction, comprising:

creating a burr hole in said cranium of said patient proximate said sagittal sinus;

inserting a distal end of a catheter through said burr hole into said sagittal sinus;

positioning said distal end of said catheter so that said distal end points generally in said upstream direction with respect to said blood flow.

2. A method of creating a sinus shunting catheter in a patient having a cranium, comprising:

inserting one end of a catheter into said proximate a ventricle of said patient;

coupling a valve in said catheter;

inserting an opposite end of said catheter into said cranium proximate a superior sagittal sinus, said superior sagittal sinus having blood flow from an upstream direction to a downstream direction; and positioning said catheter so that said opposite end points generally in said upstream direction with respect to said blood flow.

3. A method as in claim 2 wherein said catheter has a sinus portion between said valve and said opposite end of said catheter and wherein said sinus portion of said catheter has at least a ninety degree bend.

4. A method as in claim 3 wherein said sinus portion of said catheter has approximately a one hundred eighty degree bend.

5. A method as in claim 4 wherein said one hundred eighty degree bend occurs approximately 7 to 11 centimeters from said opposite end of said catheter.

6. A sagittal sinus shunt, comprising:

a catheter having a ventricle portion and a sinus portion, said ventricle portion adapted for placement into a cranium of a patient proximate a ventricle and said sinus portion adapted for placement into said cranium of said patient proximate a superior sagittal sinus; and a valve operatively coupled in said catheter between said ventricle portion and said sinus portion;

said sinus portion of said catheter having approximately a one hundred eighty degree bend.

7. A sagittal sinus shunt as in claim 6 wherein said sinus portion of said catheter is formed of a semi-rigid material.

8. A sagittal sinus shunt as in claim 7 wherein said sinus portion of said catheter has a durometer of approximately eighty (80).

9. A sagittal sinus shunt as in claim 6 wherein said one hundred eighty degree bend occurs approximately 7 to 11 centimeters from said opposite end of said catheter.

10. A sagittal sinus shunt as in claim 6 wherein said sagittal sinus has blood flow from an upstream direction to a downstream direction and wherein a distal end pf said sinus portion of said catheter is positioned generally in said upstream direction with respect to said blood flow.

* * * * *